United States Patent [19]

Cottingham

[11] 4,216,775
[45] Aug. 12, 1980

[54] ELECTROLYSIS HAIR REMOVAL APPARATUS

[75] Inventor: Hugh V. Cottingham, Upper Montclair, N.J.

[73] Assignee: Inverness International Corporation, Englewood, N.J.

[21] Appl. No.: 964,866

[22] Filed: Nov. 30, 1978

[51] Int. Cl.³ .......................................... A61B 17/36
[52] U.S. Cl. ............................. 128/303.18; 116/140; 340/573; 340/692
[58] Field of Search ...................... 128/303.18, 303.13, 128/303.14, 303.17, 303.1; 116/140, 22 R, 24; 340/573, 692

[56] References Cited

U.S. PATENT DOCUMENTS

| | | | |
|---|---|---|---|
| 3,054,405 | 9/1962 | Tapper | 128/303.18 |
| 3,315,678 | 4/1967 | Donelson | 128/303.18 |
| 3,359,982 | 12/1967 | Guiorguiey | 128/303.18 |
| 3,961,630 | 6/1976 | Gonser | 128/303.14 |
| 3,979,657 | 9/1976 | Yorksie | 340/692 X |
| 4,031,898 | 6/1977 | Hiltebrandt et al. | 128/303.1 |

FOREIGN PATENT DOCUMENTS 855459  11/1960  United Kingdom ............... 128/303.17

*Primary Examiner*—Lee S. Cohen
*Attorney, Agent, or Firm*—Blum, Kaplan, Friedman, Silberman & Beran

[57] ABSTRACT

An electrolysis hair removal apparatus including a stylet adapted to be placed in contact with a papilla to effect destruction of same and further including an indicator for indicating the optimum position of the stylet and the duration that the stylet should remain in such optimum position during each electrolysis hair removal operation is provided. The stylet is coupled through a voltage source to a conductive reference member. A detection circuit is adapted to produce a detection signal when the stylet is selectively positioned at the papilla. A first indication circuit, in response to the detection signal, is adapted to produce a first indication signal representative of the optimum positioning of the stylet. A delay indication circuit, in response to said detection circuit producing a detection signal, is adapted to produce a second indication signal representative of the completion of the hair removal electrolysis operation at a predetermined interval of time after the first indication signal.

23 Claims, 7 Drawing Figures

ELECTROLYSIS HAIR REMOVAL APPARATUS

BACKGROUND OF THE INVENTION

This invention is directed to an electrolysis hair removal apparatus including an indication circuit and, in particular, to an electronic hair removal apparatus including an indication circuit for indicating when the stylet is disposed in contact with a papilla to effect destruction of same, and for further indicating the duration of time required to complete the destruction of the papilla.

In theory, electrolysis hair removal operations have been designed to destroy the papilla (bulb) which is located within the skin's pore. Each hair in the human body grows from a papilla which is living tissue at the end of each hair. Moreover, sweat glands surround the papilla within the pore and keep the papilla moist.

In the past, electrolysis hair removal devices have operated by effecting a two part operation. The first part is the electrolysis of salt that is produced by the sweat glands. Specifically, by electrolyzing the salt (sodium chloride, $Na^+Cl^-$) into lye (sodium hydroxide, $Na^+OH^-$). The lye then dissolves the hair and allows the removal of same without destruction of the papilla. It is noted, however, that if the papilla is disrupted during this operation, the growth of a plurality of hairs or hair that is of a more coarse texture will likely result. The second part of the hair removal process is known as electrocoagulation (electrodenaturing) of the small blood vessels which feed the papilla. Electrocoagulation is utilized to cut off the blood flow to the papilla and kill same, thereby impeding the growth of hair. Because the papilla is the only part of the hair that grows, once it is coagulated, the hair growing therefrom can then be removed by a tweezer.

Heretofore, the simplest to operate and least expensive to manufacture electrolysis device was disclosed and claimed in U.S. Pat. No. 3,054,405 (Tapper). The Tapper device is no more than a probe including a spring loaded stylet, a conductive probe handle and an insulator disposed intermediate the stylet and the probe handle in order to insure insulation therebetween. In the commercial verson of the Tapper device, the negative terminal of a DC battery is coupled to the stylet and the positive terminal of the battery is coupled to the probe. In accordance with the foregoing description of the theory of hair removal, the stylet is inserted into the pore and upon being positioned substantially in contact with the papilla, performs the electrolysis of the salt and the electrocoagulation discussed above.

It is noted, however, that in order to properly perform the electrolysis of salt and electrocoagulation required to successfully effect hair removal, the probe and, in particular, the sytlet thereof must be properly positioned. Improper positioning of the probe can result in a treatment which has the final result of an increase in the growth of hair or in a treatment which causes trauma and injury to the person being treated. For this reason, the positioning of the probe has been the domain of electrolysis operators which many States require to be licensed. This is particularly the case in the Tapper device because of the spring loading of the stylet. Specifically, if the stylet of the Tapper device is placed in contact with the skin, near the base of the hair canal, as the area around the stylet coagulates, the spring biasing pressure on the stylet can break the skin and thereby cause bleeding.

A second problem with the Tapper device and those of its genre is that the electrolysis operation performed thereby must be limited to a certain period of time, such as forty-five seconds, resulting in two distinct disadvantages. The first disadvantage is that a person attempting to operate the Tapper device on his own or, alternatively, a trained operator, must concentrate on positioning the stylet in the pore, in contact with the papilla and, yet, simultaneously monitor the time of the electrolysis operation. Optimally positioning the stylet in contact with the papilla during the entire electrolysis operation is sufficiently difficult even without having to divert the operator's attention to a timing device. Also, while such timing takes place, the electrolysis operator cannot be certain that the stylet is in optimum contact with the papilla. Both of these disadvantages render the Tapper device less than completely satisfactory. The instant invention is, therefore, characterized by an electrolysis hair removal apparatus that can eliminate the above noted disadvantages.

SUMMARY OF THE INVENTION

Generally speaking, in accordance with the instant invention, an electrolysis hair removal apparatus including an indication circuit for providing an indication of the optimum positioning of a stylet in contact with a papilla and a further indication of the duration that the stylet is in contact with the papilla is provided. The electrolysis apparatus includes a conductive reference member and an insulating medium intermediate the reference member and the stylet. A voltage supply is coupled to the stylet and the reference member in order to effect a potential difference therebetween. A detector circuit is adapted to detect when the stylet is selectively positioned near the papilla and, in response thereto, produce a detection signal. A first indicator circuit is coupled to the detector circuit and is adapted to produce a first indication signal in response to the detection signal being applied thereto. A delay indicator circuit is coupled to the detector circuit and, in response to the detection signal, is adapted to produce a second indication signal at a predetermined interval of time after the first indication signal is produced.

In a preferred embodiment of the instant invention, the first indicator circuit will produce a high frequency indication signal capable of driving an audio transducer to produce a first audio signal indicating the optimum placement of the stylet in substantial contact with the papilla. The delay indicator circuit will then, after a predetermined time interval, produce a second indication signal for intermitting the first audio signal thereby causing the audio transducer to emit a second distinct audio signal indicating that the stylet should be removed from the pore.

Accordingly, it is an object of the instant invention to provide an improved electronic electrolysis hair removal apparatus.

A further object of the instant invention is to provide an electrolysis hair removal apparatus that indicates when the apparatus is optimally positioned with respect to the papilla for performing an electrolysis operation.

Still a further object of the instant invention is to provide an electrolysis hair removal apparatus that indicates when the papilla has been detected and, hence, that the electrolysis operation is being performed.

Still another object of the instant invention is to automatically provide an indication that the electrolysis operation is completed.

Still other objects and advantages of the invention will in part be obvious and will in part be apparent from the specification.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

Figure 1:
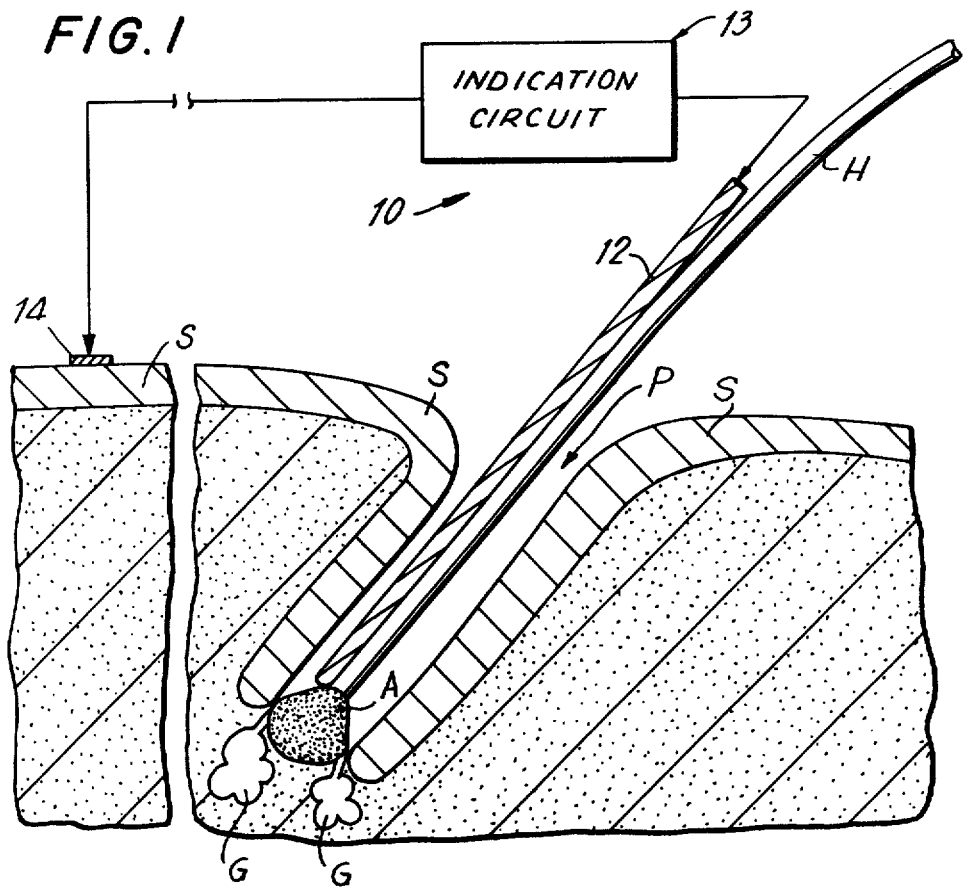
FIG. 1 is a schematic illustration of an electrolysis hair removal apparatus constructed in accordance with a preferred embodiment of the instant invention.

Reference is first made to FIG. 1, wherein an electrolysis hair removal apparatus, generally indicated as 10, is depicted. The electrolysis apparatus includes a conductive stylet 12 coupled through an indication circuit, generally indicated as 13, to a reference conductor 14. As will be explained in greater detail below, the indication circuit includes a DC voltage supply for delivering a DC potential to the reference conductor 14 and conductive stylet 12. Although not limited thereto, the stylet 12 and reference conductor 14 can be formed in the shape of a probe having a spring biased conductive stylet, a conductive outer surface defining the reference conductor and an insulator between the outer surface of the probe and the conductive stylet in the same manner disclosed in aforementioned U.S. Pat. No. 3,054,045, which patent is incorporated by reference for this purpose as if fully set forth herein. As will be discussed in detail below with respect to the operation of the electrolysis apparatus 10, the conductive stylet 12 is illustrated in a position wherein same is inserted in a pore P having a papilla A formed therein with a hair H growing therefrom. The reference conductor 14 is illustrated in contact with the skin S. Sweat glands G are located at the junctions where skin S and the papilla A are adjacent each other.

Figure 2:
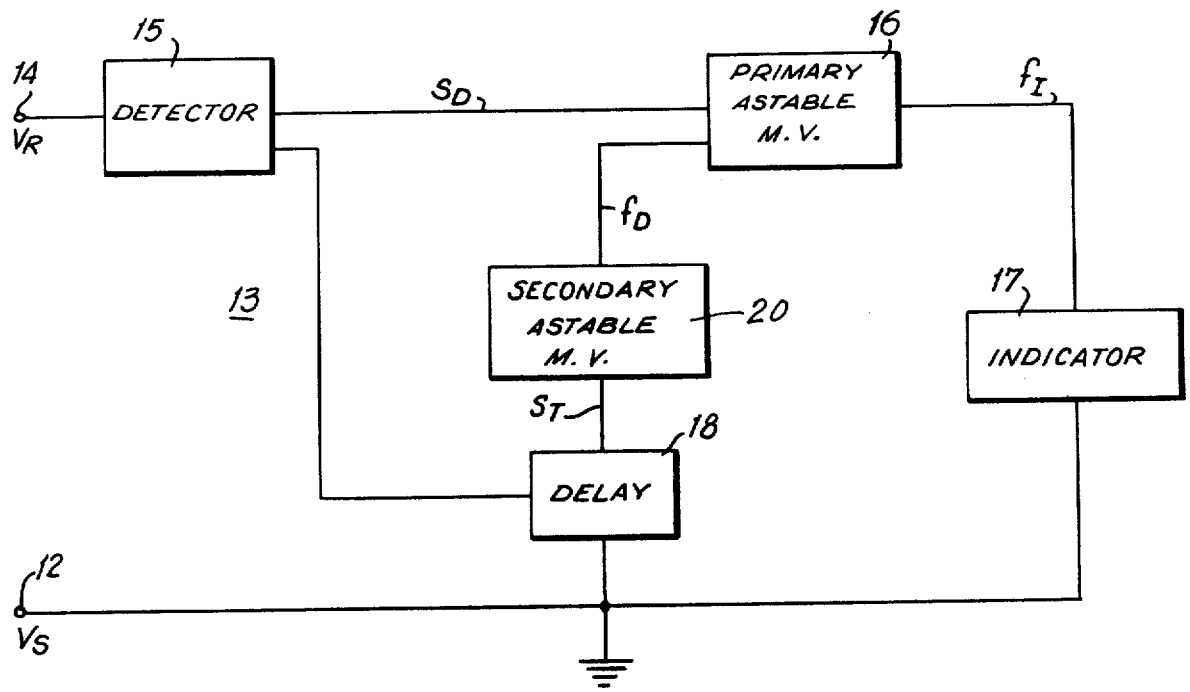
FIG. 2 is a block circuit diagram of the indication circuit included in the electrolysis hair removal apparatus depicted in FIG. 1.

Referring now to FIG. 2, a block circuit diagram of the indication circuit 13 and the manner in which same is coupled to the reference conductor 14 and stylet 12 is depicted. The indication circuit includes a detector 15 referenced to the reference conductor $V_R$. Detector 15 is adapted to detect when the stylet 12 is disposed in contact with the papilla and, in response thereto, apply a detector signal $S_D$ to a primary astable oscillator 16. The primary astable oscillator 16, in response to the detection signal $S_D$, is adapted to produce a 450 Hz high frequency indication signal $f_I$, which signal is applied to an indicator 17 to thereby activate same. If the indicator 17 is an acoustic transducer, such as a piezoelectric crystal, a first acoustic signal in the form of a hum will be produced in response to the frequency of the indication signal being on the order of 450 Hz. Accordingly, in a preferred embodiment, indicator 17 will provide an acoustic signal indicating that the stylet is in optimum contact with the papilla. A delay circuit 18 is coupled between the detector 15 and ground and, in response to detecting the presence of detection signal $S_D$, after a predetermined interval of time, such as 45 seconds, the delay circuit will apply a delay signal $S_T$ to a secondary astable oscillator circuit 20. The secondary astable oscillator circuit 20, in response to receiving the delay signal $S_T$, produced by delay circuit 18, will apply a delay indication signal $f_D$, having a frequency on the order of 8 Hz, to the primary astable oscillator 16. The primary astable oscillator 16, in response to every other half cycle of the delay indication signal, will be inhibited from producing the intermediate frequency signal and will, therefore, produce an intermittent 450 Hz signal that will cause the indicator 17 to intermit and, hence, in the case of an acoustic transducer, produce a beeping sound that is clearly distinct from the original humming sound produced by the indicator when the indication signal $f_I$ was continuously applied thereto.

Accordingly, the operation of the electrolysis hair removal apparatus, depicted in FIGS. 1 and 2, is as follows. In response to the reference conductor 14 being disposed in contact with a person's skin S, and the stylet being disposed in contact with the papilla A, for the reasons detailed at length below, an increase in the flow of current occurs at the stylet and reference conductor, thereby actuating detector 15. As aforenoted, in response to being actuated, the detector 15 applies detection signal $S_D$ to the primary astable oscillator 16 in order to effect actuation of the indicator 17 by the application of indication signal $f_I$ thereto. Indicator 17 will therefore provide a first indication of the increase in current at the stylet, which increase only occurs as a result of contact with the papilla being made by the stylet. Thus, the first humming sound made by the indicator 17 tells the operator that proper contact with the papilla has been made and that the electrolysis operation has begun. The delay circuit 18 is actuated at the same time that indicator 17 is actuated and, forty-five seconds later, produces a delay signal $S_T$ which actuates a second astable oscillator 20. Once actuated, the secondary astable oscillator 20 will produce a delay indication signal, which signal varies the output of the primary astable oscillator and causes an intermittent hum to be produced by the acoustic indicator 17, which intermittent hum is perceived by the listener as a beeping sound. Thus, in response to the second acoustic sound, namely, the beeping signal, the operator is apprised of the completion of the electrolysis operation and is therefore reminded to remove the stylet from the pore.

Figure 4:
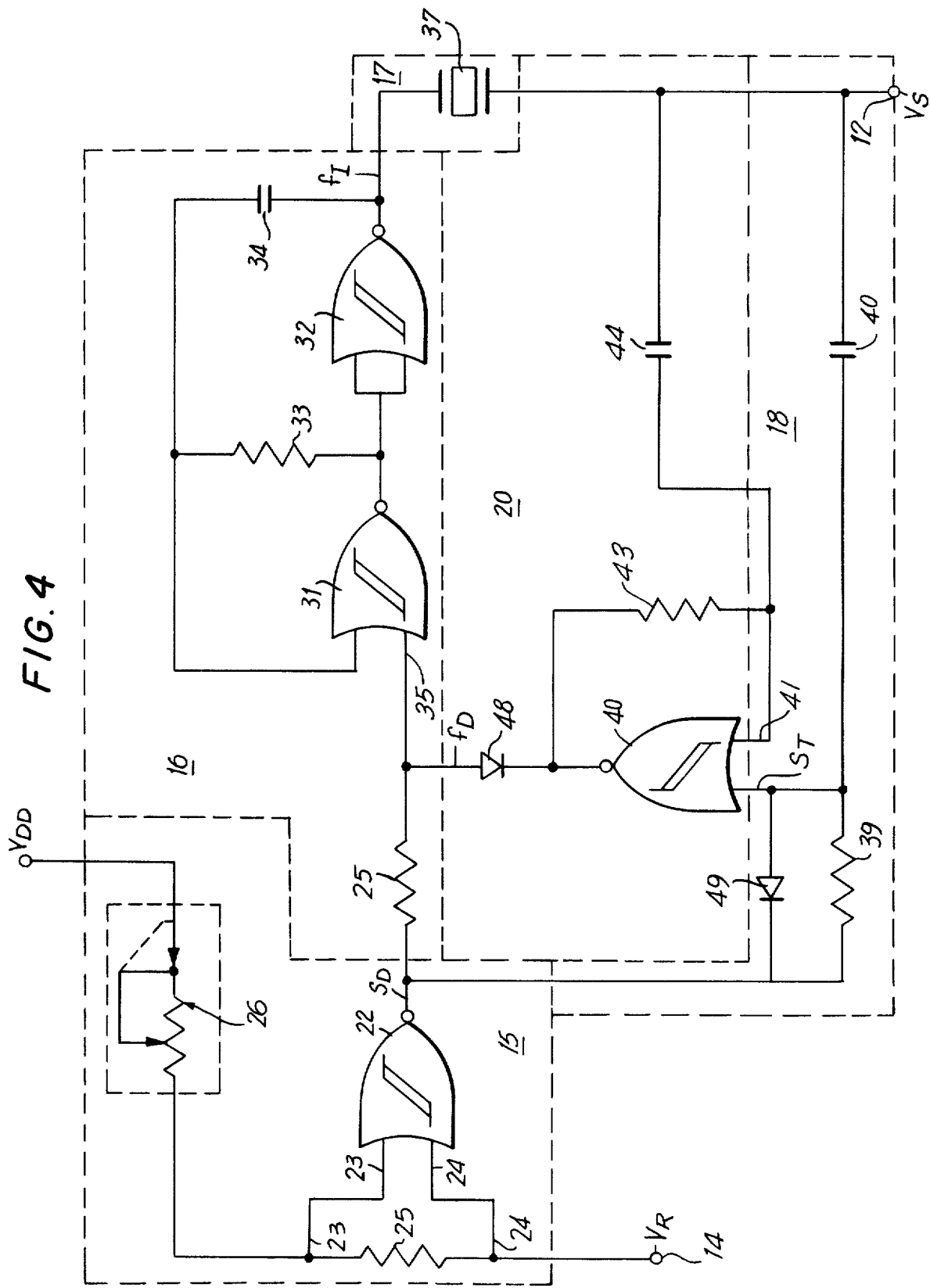
FIG. 4 is a circuit diagram illustrating an acoustic indication circuit constructed in accordance with an exemplary embodiment of the instant invention.

Reference is now made to FIG. 4, wherein a detailed circuit, representative of an exemplary embodiment of the indication circuit 13, is depicted. It is noted that the detector circuit 15 is comprised of Schmitt NAND gate 22, having a first input 23 and a second input 24. Input 24 is directly coupled to the reference conductor whereas input 23 is coupled through a resistor 25 to the reference conductor. Additionally, the input 23 is coupled through an intensity control generally indicated as 26 to the positive terminal of a DC voltage supply $V_{DD}$. As is detailed below, the detector circuit 15 produces a HIGH output detection signal when the stylet is disposed in contact with the papilla. When the stylet is not in contact with the papilla, there is no current flow and, accordingly, inputs 23 and 24 of NAND gate 22 are both HIGH level binary inputs, thereby resulting in a LOW level binary output.

Figure 3A:
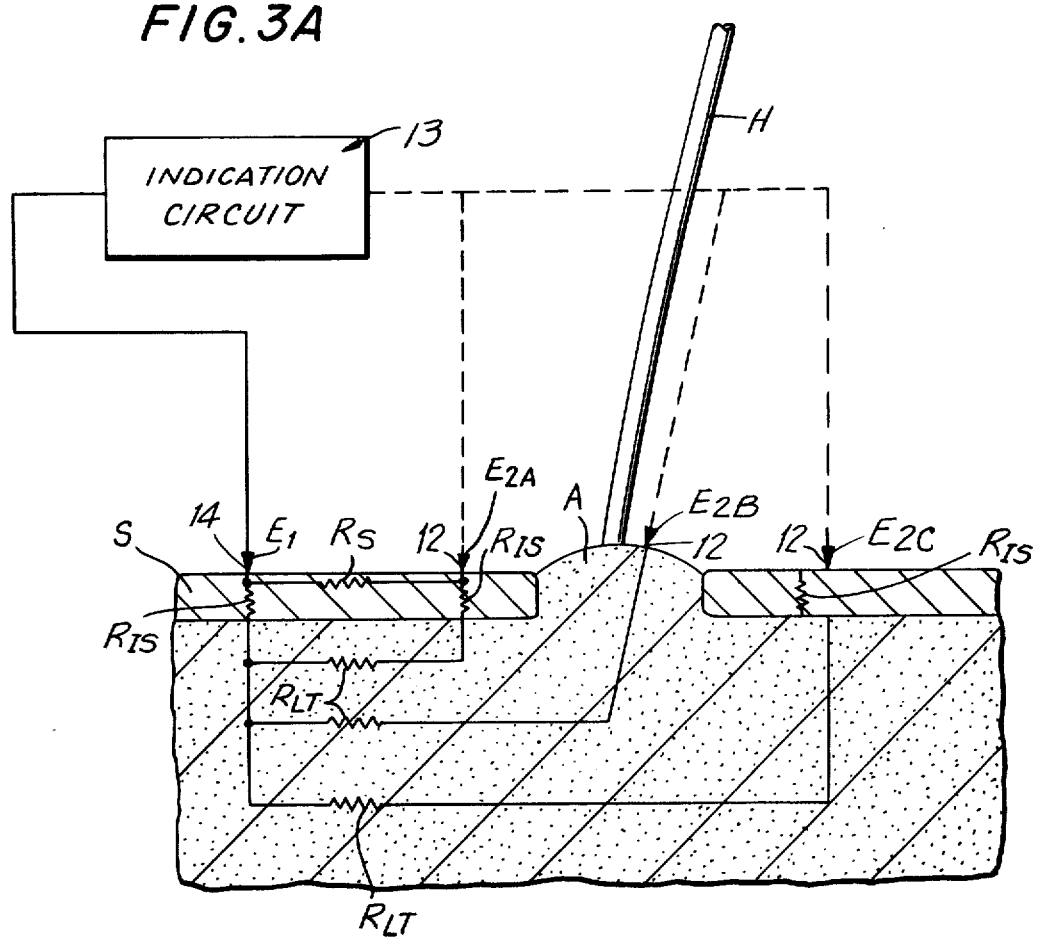
FIGS. 3A, 3B and 3C are equivalent electrical illustrations of the manner in which the electrolysis hair removal apparatus of the instant invention operates.
Figure 3B:
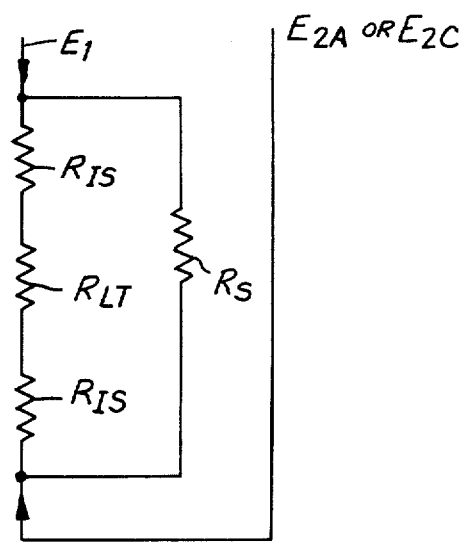

As is illustrated in FIG. 3A, since the skin S is not living tissue on the surface of the body but, instead, is composed of compacted layers of dead cells, the skin provides a high resistivity compared to the low resistivity of living tissue, which is essentially 70% water with various salts dissolved in it. Accordingly, three different stylet positions are represented by positions $E_{2A}$, $E_{2B}$ and $E_{2C}$ in FIG. 3A, with the position of the reference conductor being represented by position $E_1$. When the stylet is placed at positions $E_{2A}$ and $E_{2C}$, the equivalent circuit, illustrated in FIG. 3B, is obtained wherein $R_{IS}$ is inherent skin resistance, $R_S$ is shunt resistance, $R_{LT}$ equals living tissue resistance and $R_S >>> R_{IS} >>> R_{LT}$. In this event, the total resistance of the equivalent circuit, when the probe is not in contact with the papilla, is as follows:

$$R_T = \frac{1}{\frac{1}{2(R_{IS}) + R_{LT}} + \frac{1}{R_S}}$$

Figure 3C:
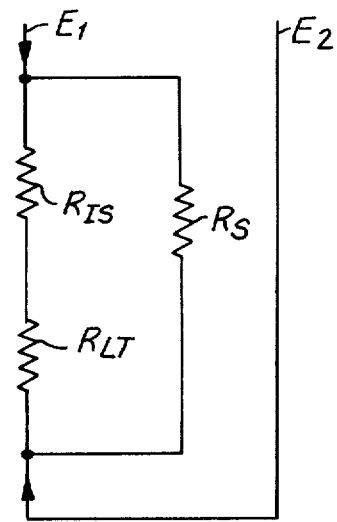

Similarly, when the stylet is positioned at location $E_{2B}$, illustrated in FIG. 3A, an equivalent circuit of the type illustrated in FIG. 3C is obtained. For this circuit, the following total resistance $R_T$ is obtained:

$$R_T = \frac{1}{\frac{1}{R_{IS} + R_{LT}} + \frac{1}{R_S}}$$

In light of the foregoing, it is apparent that the difference in the total resistance ($R_T$) when the stylet is positioned in contact with the skin ($E_{2A}$ & $E_{2C}$) or, alternatively, when the stylet is positioned in contact with the papilla ($E_{2B}$) is equal to the skin resistance ($R_{IS}$).

Accordingly, when the stylet contacts the papilla, a large increase in the sink current at the reference electrode $V_R$ occurs due to the reduction in the skin resistance of the amount or $R_{IS}$. This raises the current level sourced at the electrode $V_R$, and, hence, references input 24 to a lower voltage level with respect to input 23 of NAND gate 22 and causes a LOW signal to be applied to input 24 of NAND gate 22 and a HIGH level detection signal $S_D$ to be produced. As aforenoted, a HIGH level detection signal $S_D$ actuates the indication circuitry to provide the respective indications in a manner to be discussed in greater detail below. Accordingly, by utilizing the increase of current sourced at the electrode $V_R$, when the stylet is brought into contact with the papilla, the detection circuit is actuated.

Figure 5:
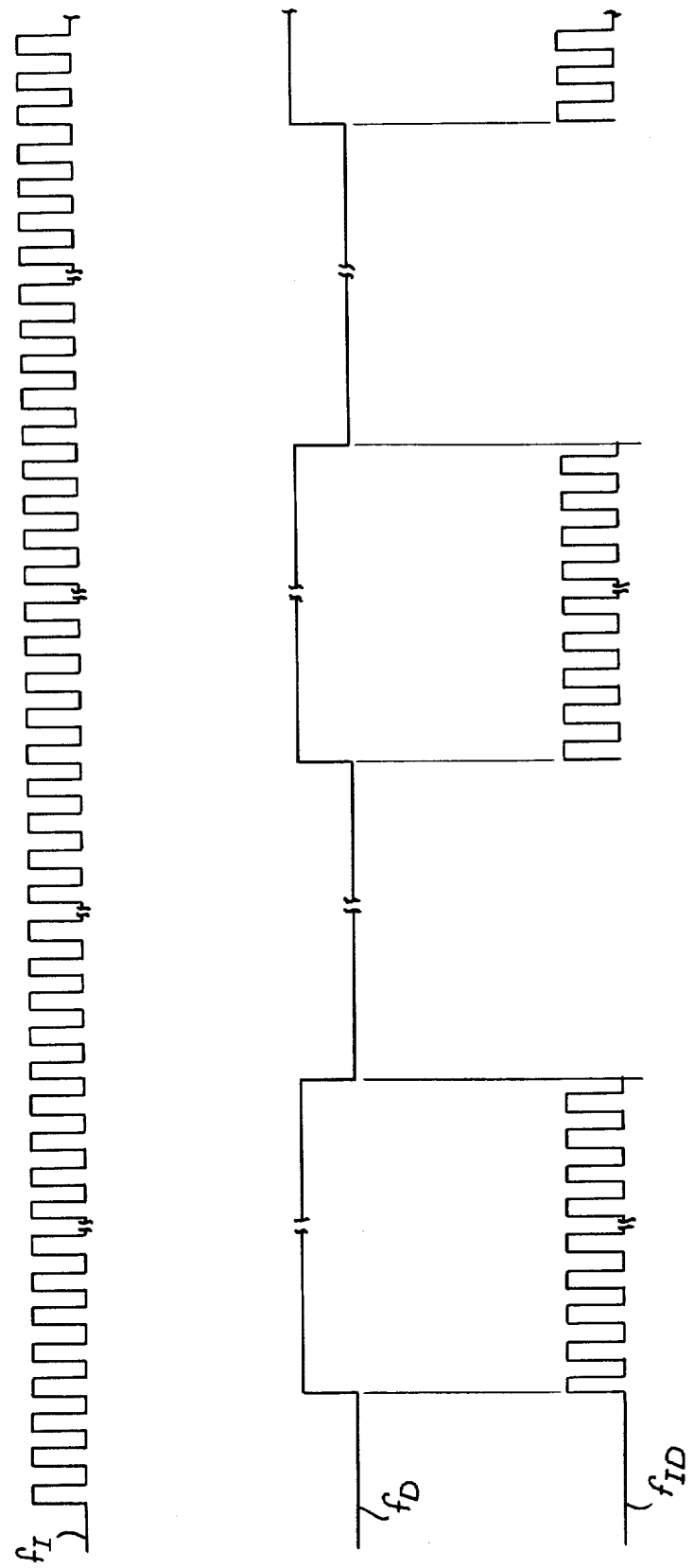
FIG. 5 is a comparative wave diagram illustrating the operation of the acoustic indication circuit depicted in FIG. 4.

Referring now to FIGS. 4 and 5, a detailed description of an indication circuit, constructed in accordance with an exemplary embodiment of the instant invention, and the manner in which same is operated as a result of the detection signal $S_D$, is provided, like reference numerals being utilized to denote like elements discussed above. When the output of NAND gate 22 becomes HIGH, in the manner noted above, a detection signal is applied through a resistor 25 to the input of Schmitt NAND gate 31 which gate, in combination with Schmitt NAND gate 32, resistor 33 and capacitor 34, define primary astable oscillator circuit 16. Oscillator circuit 16 is actuated in response to the HIGH level detection signal being applied thereto, and will produce an indication signal $f_I$ having a frequency on the order of 450 Hz. A piezoelectric audible transducer 37 produces a continuous output tone in response to the 450 Hz indication signal being applied thereto. The continuous output tone provides an indication to the operator that the papilla has, in fact, been contacted by the stylet and, hence, that the electrolysis hair removal operation has been commenced. In response to the output of NAND gate 22 being referenced to a HIGH level potential, an RC circuit, defined by resistor 39 and capacitor 40, begins to charge for a predetermined time interval determined by the time constant thereof.

In accordance with the description detailed above, the RC circuit, defined by resistor 39 and capacitor 40, provides a time constant on the order of 45 seconds. Accordingly, the RC circuit references the input 41 of Schmitt NAND gate 40 to a HIGH level at the end of the forty-five second period, to thereby actuate the secondary astable oscillator circuit comprised of NAND gate 40, resistor 43 and capacitor 44 so that same produces a delay indication signal $f_D$ having a frequency on the order of 8 Hz. Accordingly, the 8 Hz time delay indication signal $f_D$ is applied across diode 48 to input terminal 35 of the astable oscillator 16 to thereby swamp the 450 Hz signal produced by the astable oscillator 16 during each negative half cycle of the delay indication signal $f_D$. As is illustrated in FIG. 5, the delay indication signal inhibits the astable oscillator 16 during each lower half cycle thereof, and thereby causes the astable oscillator to apply an intermittent 450 Hz signal $f_{ID}$ to the audio transducer 37 and, hence, produce an intermittent beeping tone in lieu of the continuous tone previously produced thereby. The intermittent beeping tone provides a signal warning to the operator to remove the stylet from the pore and, to this end, the indication circuit will continue to produce the intermittent beeping signal until the probe is removed. Once the output of the NAND gate 22 is returned to a LOW level, by removing the stylet from contact with the papilla, both the astable oscillator circuit 16 and secondary astable oscillator circuit 20 are returned to a quiescent state and the RC circuit, defined by resistor 39 and capacitor 40, is immediately discharged through a diode 49, to thereby avoid any possible timing error when the next electrolysis hair removal operation is performed.

Accordingly, the instant invention is particularly characterized by an indication circuit that can provide a first indication representative of an increase in current caused as a result of the stylet contacting the papilla, thereby signalling the operator that the electrolysis process has begun and further producing a second indication after a predetermined interval of time to the operator that the electrolysis hair removal operation is completed. To this end, it is noted that although the preferred embodiments of the instant invention have illustrated a circuit wherein an acoustic transducer is utilized to produce two distinct sounds, it is noted that a signal lamp can be driven at a high frequency above the flicker rate so that the human eye will perceive it to be continually lit and thereafter flickered as a result of the 8 Hz signal being applied thereto in order to provide two distinct indications of the type detailed above to the operator. It is noted, however, that an acoustic indication mechanism does provide the operator with the opportunity to concentrate his or her attention on inserting the probe into the pore to commence the electrolysis hair removal operation.

Thus, the indication circuit of the instant invention simplifies the electrolysis hair removal operation by permitting the operator to concentrate on the placement of the stylet in the pore and, hence, eliminate the operator's concern that the stylet is not properly inserted into the pore when the operator is monitoring the sweep second hand of a clock and possibly damaging the skin as a result thereof. By permitting the operator to concentrate on retaining the stylet within the pore, the operator is also less likely to inadvertently remove the stylet from the pore during the forty-five second interval and, hence, not complete the electrolysis and electrocoagulation necessary to complete hair removal and destroy the papilla, which often results in the growth of multiple hairs or coarser hair.

It will thus be seen that the objects set forth above, among those made apparent from the preceding description, are efficiently attained and, since certain changes may be made in the above construction without departing from the spirit and scope of the invention, it is intended that all matter contained in the above description of shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. In an electrolysis apparatus including a conductive reference member, a conductive stylet adapted to be selectively positioned near the papilla, and a voltage supply coupled to said stylet and to said reference member, the improvement comprising, detection means operatively coupled to said reference member and stylet for detecting the presence of a papilla at said stylet when said stylet is selectively positioned at the papilla, and in response to being continuously selectively positioned at the papilla, continuously producing a detection signal, first indication means coupled to said detection means for continuously producing a first indication signal in response to said detection signal being applied thereto and delay indication means coupled to at least said detection means for producing a second indication signal at a predetermined interval of time after the occurence of said first indication signal.

2. An electrolysis apparatus as claimed in claim 1, wherein said first indication means includes a first signal means for continuously producing said first indication signal in response to said detection signal being applied thereto and an indicator coupled to said signal means for producing an indication to an operator that the stylet is in contact with a papilla when the first indication signal is applied thereto.

3. An electrolysis apparatus as claimed in claim 2, wherein said delay indication means includes a second signal means for producing a second indication signal that is distinct from said first indication signal, said indicator being adapted in response to said second indication signal being produced by said second signal means to indicate that a predetermined interval of time has elapsed.

4. An electrolysis apparatus as claimed in claim 3, wherein said first signal means in response to said second indication signal being applied thereto produces a first indication signal that is controlled by the second indication signal at the time that the first indication signal is applied to said indicator.

5. An electrolysis apparatus as claimed in claim 4, wherein said indicator is a piezoelectric quartz crystal transducer.

6. In an electrolysis apparatus including a conductive reference member, a conductive stylet adapted to be selectively positioned near the papilla, and a voltage supply coupled to said stylet and to said reference member, the improvement comprising, detection means operatively coupled to said reference member and stylet, said detection means including a gating means coupled intermediate said conductive reference member and said voltage supply for detecting the flow of current therebetween, said detection means being adapted to produce a detection signal in response to a predetermined increase in the flow of current between the voltage supply and the reference member, first indication means coupled to said detection means for producing a first indication signal in response to said detection signal being applied thereto and delay indication means coupled to at least said detection means for producing a second indication signal at a predetermined interval of time after the occurrence of said first indication signal.

7. An electrolysis apparatus as claimed in claim 6, wherein said gating means includes a logic gate having a first input referenced to said voltage supply, a second input referenced to said conductive reference member and an impedance means intermediate said first and second inputs, said impedance means being adapted to vary the voltage level between said first and second inputs, when the current flow between said reference member and said voltage supply increases, said logic gate being adapted to produce said detection signal in response to a predetemined difference in the magnitude of the voltage levels at said first input and second input.

8. An electrolysis apparatus as claimed in claim 7, wherein said logic gate produces a detection signal when the binary level of said first input and second input are distinct.

9. An electrolysis apparatus as claimed in claim 6, wherein said first indication means includes an oscillator circuit coupled to said detection means, said oscillator circuit being adapted to produce a high frequency indication signal in response to said detection signal being applied thereto and an indicator coupled to said oscillator circuit, said indicator being disposed in a first indication mode in response to said high frequency indication signal being applied thereto.

10. An electrolysis apparatus as claimed in claim 9, wherein said delay indication means includes a time delay means coupled to said detection means and said first indication means, said time delay means being adapted to provide a time delay signal at said predetermined time interval after said detection signal is produced by said detection means.

11. An electrolysis apparatus as claimed in claim 10, wherein said delay indication means further includes a second oscillator circuit for producing a low frequency sound indication signal in response to said time delay signal being applied thereto.

12. An electrolysis apparatus as claimed in claim 11, wherein said first oscillator circuit in response to said low frequency second indication signal being applied thereto swamps the higher frequency first indication signal during every other half cycle of said lower frequency second indication signal to thereby intermit said first indication signal applied to said indicator and dispose said indicator in a second indication mode.

13. An electrolysis apparatus as claimed in claim 12, wherein said indicator is an acoustic transducer, said acoustic transducer being adapted to provide a first humming sound in response to said first indication signal being applied thereto, said acoustic transducer being further adapted in response to said first indication signal being intermitted by said second indication signal to provide a beeping sound.

14. An electrolysis apparatus as claimed in claim 10, wherein said time delay means is an RC circuit coupled to said detection means, said time delay means having a discharge means coupled to at least a portion of said RC circuit in order to effect an immediate discharge thereof in the absence of a detection signal produced by said detection means.

15. An electronic indication circuit particularly suitable for use with electrolysis apparatus comprising in combination, detection means for being selectively positioned at a papilla and for continuously producing a detection signal when the detection means is selectively continuously positioned at the papilla, a first indication circuit means for continuously producing a first high frequency indication signal in response to said detection signal being applied thereto, delay circuit means coupled to said detection means for producing a second lower frequency indication signal at a predetermined interval of time after said detection signal is produced by said detection means, and indication means coupled to said first indication circuit means for being disposed into a first indication mode in response to said first higher frequency indication signal being applied thereto, said indication means being adapted to be disposed into a second indication mode in response to said second lower frequency indication signal being produced by said delay circuit means.

16. An electronic indication circuit, as claimed in claim 15, wherein said delay circuit means is coupled to said detection means and includes delay means for producing a delay signal at a predetermined interval of time after said detection signal is produced by said detection means and an oscillator means for producing said second lower frequency indication signal in response to said delay signal being applied thereto.

17. An electronic indication circuit, as claimed in claim 16, wherein said first indication circuit means is an oscillator means.

18. An electronic indication circuit, as claimed in claim 17, wherein said first indication circuit means in response to said second lower frequency indication signal being applied thereto controls the first higher frequency indication signal produced by said first indication circuit means at the time that the first indication signal is applied to said indication means.

19. An electronic indication circuit, as claimed in claim 18, wherein said indication means is a piezoelectric quartz crystal transducer.

20. An electronic indication circuit, as claimed in claim 17, wherein said first indication circuit means oscillator means in response to said low frequency second indication signal being applied thereto swamps the higher frequency first indication signal during every other half cycle to said lower frequency second indication signal to thereby intermit said first indication signal applied to said indication means and dispose said indication means in a second indication mode.

21. An electronic indication circuit, as claimed in claim 20, wherein said indication means is an acoustic transducer, said acoustic transducer being adapted to provide a first humming sound in response to said first indication signal being applied thereto, said acoustic transducer being further adapted in response to said first indication signal being intermitted by said second indication signal being adapted to provide a beeping sound.

22. An electronic indication circuit, as claimed in claim 17, wherein said delay means is an RC circuit coupled to the output of said detection means, said delay means having a discharge means coupled to at least a portion of said RC circuit in order to effect an immediate discharge thereof in the absence of a detection signal produced by said detection means.

23. An electronic indication circuit particularly suitable for use with electrolysis apparatus comprising in combination, a detection means for producing a detection signal, said detection means includes logic gate means having a first input referenced to a voltage supply, a second input and an impedance means intermediate said first and second inputs, said impedance means being adapted to vary the voltage level between said first and second inputs, when the current flow between said second input and said voltage supply increases, said logic gate means being adapted to produce said detection signal in response to a predetermined difference in the magnitude of the voltage levels at said first input and second input, a first indication circuit means for producing a first high frequency indication signal in response to said detection signal being applied thereto, delay circuit means coupled to said detection means for producing a second lower frequency indication signal at a predetermined interval of time after said detection signal is produced by said detection means, and indication means coupled to said first indication circuit means for being disposed into a first indication mode in response to said first higher frequency indication signal being applied thereto, said indication means being adapted to be disposed into a second indication mode in response to said second lower frequency indication signal being produced by said delay circuit means.

* * * * *